United States Patent [19]

Vaughan

[11] 4,322,560

[45] Mar. 30, 1982

[54] PROCESS FOR CONTROLLING HIGHLY EXOTHERMIC HYDROPEROXIDE DECOMPOSITION

[75] Inventor: Ronald J. Vaughan, Orinda, Calif.

[73] Assignee: Varen Technology, Marshallton, Del.

[21] Appl. No.: 132,149

[22] Filed: Mar. 20, 1980

Related U.S. Application Data

[63] Continuation-in-part of Ser. No. 970,474, Dec. 18, 1978, abandoned, and a continuation-in-part of Ser. No. 970,475, Dec. 18, 1978, abandoned, which is a continuation-in-part of Ser. No. 660,634, Feb. 23, 1976.

[51] Int. Cl.$^3$ ............................ C07C 45/53; C07C 37/08; C07C 29/136
[52] U.S. Cl. .................................. 568/385; 568/798; 568/840; 568/768
[58] Field of Search ............... 568/798, 768, 840, 741, 568/385; 585/709

[56] References Cited

U.S. PATENT DOCUMENTS

| | | |
|---|---|---|
| 3,037,052 | 5/1962 | Bortnick ............................ 568/798 |
| 3,169,142 | 2/1965 | Knaggs . |
| 3,784,399 | 1/1974 | Grot .................................. 117/62.1 |
| 3,959,381 | 5/1976 | Arkell ................................ 568/798 |
| 3,976,704 | 8/1976 | Vaughan . |
| 4,038,213 | 7/1977 | McClure et al. ................... 252/430 |
| 4,147,726 | 4/1979 | Wu ..................................... 568/768 |
| 4,188,308 | 2/1980 | Vaughan ............................ 252/413 |
| 4,207,264 | 6/1980 | Anderson et al. ................. 568/768 |
| 4,210,606 | 7/1980 | Austin et al. ...................... 568/798 |

OTHER PUBLICATIONS

Kapura et al., "Ind. Eng. Chem. Prod. Res. Dev.", vol. 12 (1973), pp. 62–66.

*Primary Examiner*—Werren B. Lone
*Attorney, Agent, or Firm*—Charles J. Tonkin

[57] ABSTRACT

Exothermic hydroperoxide decomposition reactions catalyzed by solid polymeric acid catalysts are controlled by contacting the reactants with a thin film of the acid catalyst supported on the surface of an impermeable heat exchanger element and contacting the opposite side of the heat exchanger element with a heat transfer fluid.

8 Claims, No Drawings

PROCESS FOR CONTROLLING HIGHLY EXOTHERMIC HYDROPEROXIDE DECOMPOSITION

This patent application is a continuation-in-part of U.S. Ser. No. 970,474, filed Dec. 18, 1978 now abandoned and U.S. Ser. No. 970,475, filed Dec. 18, 1978 now abandoned which in turn is a continuation-in-part of U.S. Ser. No. 660,634, filed Feb. 23, 1976, all in the name Ronald J. Vaughn.

FIELD OF THE INVENTION

This invention relates to the control of exothermic reactions catalyzed by solid polymeric acid catalysts and more particularly to decomposition of organic hydroperoxides.

BACKGROUND OF THE INVENTION

In most chemical reactions the distribution of reaction products (i.e., yield to desired and undesired products) is affected by reaction temperature. In highly exothermic reactions, the heat of reaction must be removed at its rate of formation to maintain a constant temperature of reaction. Many reactions catalyzed by strong acids (e.g., sulfuric, fluorosulfonic, solid polymeric acids and the like) are highly exothermic and require good control of the reaction temperature to obtain high yields of desired products and to minimize side reactions leading to charring and/or formation of tars or other undesired results.

In reactions catalyzed by liquid or gaseous acid catalyst, the catalyst can be molecularly mixed or dispersed with the reactants and the heat of reaction can be removed in conventional heat exchangers in or outside the reaction zone. With good mixing in such fluids reactions, the heat of reaction can be readily distributed from the site of reaction throughout the reaction environment, substantially at its rate of formation, and the bulk temperature and the temperature at the site of reaction can be approximately the same. It is common in highly exothermic decomposition of peroxides employing sulfuric acid as the catalyst to use a large volume of the sulfuric acid and to meter the reactants into the sulfuric acid to control the extent and rate of heat formation to effect a minimum range of reaction temperature. In addition, it is common to use an inert fluid or excess of one reactant as a heat sink and reaction rate modifier.

In contrast to liquid and gaseous catalysts in fluid or homogeneous systems, solid polymeric catalysts cannot be molecularly dispersed or dissolved in the reactants and the reactants cannot be readily metered to and from an immobile catalyst fixed in a solid polymer matrix. When using a solid polymeric acid catalyst, it is believed that the reaction takes place at the catalyst sites (i.e., small clusters of acidic groups) which are immobilized by the polymer matrix. If the heat of reaction is not removed substantially at the rate of formation, a large increase in temperature could occur at the site resulting in loss of yield of desired products and/or charring of reactants and products which can reduce the utility of the catalyst. The removal of the heat of reaction from the immobilized catalyst sites in a polymer matrix depends on the diffusivity of the reactants, diluents and reaction products in the polymeric matrix and the thermal conductivity (coefficient of heat transfer) of the polymeric matrix. Since methods commonly used to remove heat of reaction and control reaction temperature is substantially homogeneous (liquid or gaseous reactants and catalyst) reaction environments are not readily applicable to reaction environments which are hetereogeneous (solid catalyst and liquid or gaseous reactants and products), attempts have been made to adapt the methods commonly used in the homogeneous systems to the hetereogeneous systems. For example, heat exchanger elements have been immersed in a bed packed with granular ion exchange resins; and granular or powdered ion exchange resins have been slurried with the reactants and diluents and the hetereogeneous mixture passed through a heat exchanger.

SUMMARY OF THE INVENTION

The present invention provides an improved reaction system which is especially useful for carrying out solid acid catalyzed exothermic decompositions of hydroperoxides; such improved reaction system comprises a solid polymeric acid on the surface of a heat exchanger element which is substantially impermeable to the reaction environment and a coolant fluid in contact with the heat exchanger element. Further the invention is directed to a form of solid acid catalyst which permits better utilization of the catalyst sites and facilitates control of the reaction environment and removal of the heat of reaction, by providing the polymer acid catalyst as a thin film adapted for contact with the reactants and in which the thin film of catalyst is on a substantially impermeable support adapted for contact with a coolant for removing the heat of reaction. This new system is especially applicable to the acid catalyzed decomposition of hydroperoxides, particularly in a continuous process wherein the hydroperoxide is passed over the surface of the thin film of acid catalyst on the heat exchanger element and heat of reaction is withdrawn by passing a heat transfer fluid over the opposite side of the catalyst-supporting heat exchanger element.

The use of a thin film of solid catalyst on the heat exchanger support is advantageous in that thereby dependence on diffusion of reactants, diluents and products to and from catalyst sites in the solid polymeric matrix is minimized, and the number of catalyst sites near and on the surface of the thin film is greater per unit weight of the solid polymeric acid catalyst which both facilitates removal of heat of reaction from the catalyst sites to a heat exchange fluid and access of the reactants to the catalyst sites. This can result in better catalyst utility and lower cost of catalyst in materials manufacture.

The advantages of using a solid polymeric acid catalyst instead of corrosive liquid and gaseous acid catalysts include: ease and lower cost of materials separation, lower cost materials of construction, reduction in waste products such as spent and contaminated sulfuric acid and reduction in the cost of disposal of the waste products to minimize pollution of the environment.

With respect to the acid catalyzed decomposition of peroxides, the present process avoids the necessity of using solvents or diluents to absorb the heat of reaction which use leads to increased processing costs such as from the subsequent separation of the desired products from the solvents.

DETAILED DESCRIPTION OF THE INVENTION

The invention resides in the process of decomposing organic hydroperoxides by contacting said hydroperoxides with a thin film of solid polymeric acid catalyst supported on a substantially impermeable heat exchanger element which is in contact with a heat transfer fluid for removing heat of reaction generated at the active catalyst sites in the thin film. Particularly efficient temperature control of the exothermic reaction is obtained by contacting the organic peroxides with the preferred perfluorocarbon catalyst sulfonic acid on one side of a thin wall catalyst support and removing the exothermic heat of reaction by contacting the other side of the thin wall catalyst support with a heat transfer fluid. In such a reactor system, the heat transfer fluid is brought into contact with the catalyst support at a temperature and rate sufficient to remove excess heat and maintain reaction temperature control. The rates and temperatures for the heat transfer fluid will depend upon the thickness of the catalyst support (and its heat transfer coefficient) and the amount of heat generated in the decomposition reaction. Thin films of peroxide flowing over the catalytic surface allow the heat of reaction to be removed from the bulk more readily; higher flow rates of the reactants over the catalyst surface will not lead to an increased rate of reaction (due to the limited number of available catalytic sites) thus leading to moderation of the exothermic reaction.

The catalyst is any solid, stable polymer having pendant catalytically active acid groups such as sulfonic and/or carboxylic acid groups. The catalyst broadly comprises a polyfluorinated polymer having acid groups in the amount of about 0.01 to 5 mequiv/gram catalyst and preferably about 0.05 to 2 mequiv/gram. Preferred are the perfluorocarbon polymers having pendant sulfonic acid groups. The perfluorocarbon polymer is a perhalocarbon polymer containing up to 25% chloro substitution on the carbon chain. The remainder of the halo substituents are fluoro. The polymer has pendant active sulfonic acid groups and is composed of perfluorocarbon chain which preferably contains ether linkages, the chain being essentially inert.

Useful perfluorocarbon sulfonic acid polymers and their preparation are described in U.S. Pat. Nos. 3,041,317; 3,282,875; 3,624,053 and 3,882,093, the disclosures of which are hereby incorporated by reference. Perfluorocarbon sulfonic acid polymers and derivatives, referred to under the duPont tradename, NAFION resin, are described in duPont's magazine "Innovation" Volume 4/No. 3/Spring 1973 at pages 10-13.

Preferred are the perfluoro copolymers of tetrafluoroethylene or other perfluoro alpha olefins and perfluorocarbon vinyl ethers containing sulfonic acid groups. Catalysts of the above-noted structure typically have a molecular weight of between 1000 and 500,000 daltons. The equivalent weight of the preferred copolymer generally ranges from 600 to 2500, most preferably from 800 to 1500; equivalent weight is defined as the average molecular weight per sulfonic acid group in grams. Most preferred are the copolymers of the tetrafluoroethylene and perfluorovinyl ethers containing sulfonic acid groups, which copolymer would have the following repeating structure:

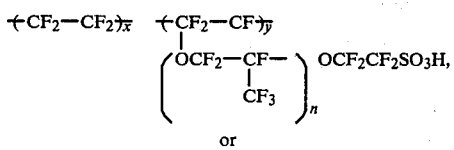

or

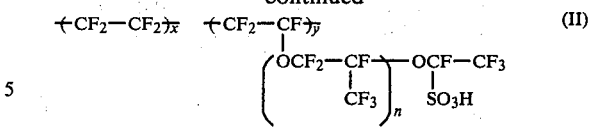

or mixtures thereof, where n is 1 or 2 and x over y ranges from 2 to 50.

Generally, other solid sulfonated or other acid catalysts can also be used. For example, the sulfonated polystyrene catalysts and sulfonated copolymers of ethylene and methacrylic acid such as those described in U.S. Pat. Nos. 3,037,052; 3,017,441 and 3,239,575 can be used in the present process; however, they are generally less stable and hence are less preferred than the perfluorocarbon polymer sulfonic acid catalysts described above. The preferred sulfonated perfluorocarbon polymer catalysts also offer the advantages of high concentrations of accessible acid groups in a solid phase. Further these preferred catalysts can be readily regenerated, especially by the method of my U.S. Pat. No. 4,188,308.

Since the preferred perfluorosulfonic acid catalysts employed in the present invention are not soluble and are essentially infusible, they have the advantages of being stable and not readily leached from their supports. A fabricable intermediate which is fusible or soluble is first prepared, then shaped into the desired form and thereafter converted to generate the active sulfonic acid groups, as disclosed in my copending application U.S. Ser. No. 970,475, filed Dec. 18, 1978, the disclosure of which is hereby incorporated by reference. A particularly preferred intermediate is the copolymer of tetrafluoroethylene and perfluorovinyl ether containing sulfonyl fluoride groups, which copolymer would have the following illustrative repeating structure:

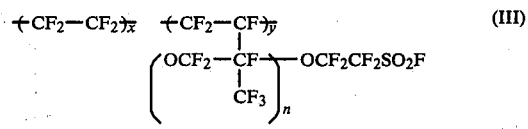

wherein n is 1 or 2, and the ratio of x over y is between 2 and 50. These sulfonyl fluoride derivatives are readily converted, preferably via the alkali metal sulfonate derivatives to the fusible quaternary ammonium and phosphonium sulfonate derivatives. After forming the thin film of catalyst precursor, it is converted to the active acid form such as treatment with an appropriate acid. The equivalent weight of the preferred perfluorovinyl ether-tetraethylene copolymer preferably ranges from 850 to 2500 where the equivalent weight is defined as the average mole weight per sulfonyl group. If the sulfonyl fluoride precursor is used as the support, the surface thereof can be treated so as to convert only a thin surface layer to the active sulfonic acid form.

The preferred perfluorovinyl ethers used in the copolymer of the above formula III can be polymerized, as described more fully in Connolly et al, U.S. Pat. No. 3,282,875, in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from −50° C. to +200° C. depending on the initiator used. Pressure is not critical and is generally employed to control the ratio of the gaseous comonomer to the fluorocarbon vinyl ether. Suitable fluorocarbon solvents are known in the art and are generally perflucroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of the above structures in an aqueous medium using a peroxide or a redox initiator. The polymerization methods employed correspond to those established in the art for the polymerization of tetrafluoroethylene in aqueous media.

A thin film of the solid polymeric acid catalyst is supported on the surface of an impermeable heat exchanger element. The thin film is usually of minimal thickness so as to reduce the amount of diffusion of the reactants and products through the catalyst matrix. Preferably the thickness of the catalytic polymer surface varies from essentially a molecular thickness up to a thickness of 10 mils. Most preferably, the thickness is no more than 2 mils. Since the support is essentially impermeable and normally inert the film need not be free of holes and indeed may be discontinuous so long as there are an adequate number of active catalyst sites to promote the desired reaction. Optionally, the film of solid polymeric acid catalyst can be modified by incorporating metals, metal oxides and compounds which are homogeneous catalysts.

The heat exchanger element can be of any material which is essentially impermeable and which provides support for the catalyst in a heat exchange relationship with a coolant or heat transfer fluid as will be readily understood by one skilled in the art.

As indicated above, a preferred heat exchange system combines in one element a surface having catalytic activity with a surface having heat exchange capability. The surface of the heat exchange portion must be stable to the fluid being used to remove heat from the reaction zone. The heat transfer fluid can be any of those fluids well known in the art for their ability to transport heat. These include water, oil, air, and the like.

The reactor-exchanger can be single or multiple elements of tubes, hollow fibers and sheets with tube sheets, shells, headers and other fittings as necessary so that the reactants contact the catalytic surface and are separated from the coolant which contacts the other surface of the elements. Tubes and hollow fibers can be formed into conventional-type fluid heat exchangers—with tube sheets, headers, shells and fluid inlets and outlets. Tubes and fibers can also be immersed into the reaction medium wherein the catalytic surface is on the outer surface of the fibers or tubes and the coolant is in the bore of the tube, and the opposite arrangement. When using flat sheets, the sheets can be formed into a filter press plate and frame arrangement with spacers and controlled flow channels for reactants and coolants.

The dimensions of the tubes, hollow fibers and sheets can vary over a wide range as necessary to achieve optimum processing conditions. In general, the thickness dimension would be controlled to a minimum value to effect maximum heat removal consistant with adequate separation of the reaction medium and coolant.

As will be apparent to one skilled in the art, various materials can be used for the heat exchanger elements, including metallic, ceramic and polymeric. Materials such as brass and copper which have high thermal conductivities will normally be used. The surface of the heat exchanger element exposed to the heat transfer fluid will be preferably corrosion resistant and can be treated to increase its wetting characteristics, thereby increasing the efficiency of the heat transfer fluid.

Thus, one embodiment of this invention comprises a solid polymeric acid catalyst suitable for carrying out highly exothermic organic hydroperoxide decompositions under controlled conditions, consisting essentially of a thin film of said catalyst adapted for contact with the reactants in the acid catalyzed reaction and in which said thin film of catalyst is on an impermeable support, i.e., a heat exchanger element, adapted for contact with a coolant, i.e., heat transfer fluid, for removing heat of reaction.

Preferred because of their commercial utility are the aliphatic (including cyclo- and aryl-substituted aliphatic) hydroperoxides, particularly the secondary and tertiary hydroperoxides. Included, for example, are the phenyl alkyl hydroperoxides of 8–12 carbon atoms such as to methyl benzyl hydroperoxide and cumyl hydroperoxide, cycloaliphatic hydroperoxides such as cyclohexyl hydroperoxide, and alkyl hydroperoxides in which the alkyl group is a tertiary butyl and like alkyl groups.

The hydroperoxides will decompose by the use of the process of the present invention in the manner that hydroperoxides decompose in acid catalyzed decompositions as well known in the art (see, for example, "Organic Peroxides" by E. G. Hawkins, published by E & F Spon, Ltd., 1961 and "Principles of Organic Synthesis"). However, in view of the ability of the present invention to readily control the temperature, less side reactions occur and thereby less by-products are produced. For example, the decomposition products of cumyl hydroperoxide will be mostly phenol and acetone, for cyclohexyl hydroperoxide mostly to cyclohexanol and cyclohexanone, for $\alpha$-methyl benzyl hydroperoxide mostly to acetaldehyde and phenol and tertiary butyl hydroperoxide mostly to acetone and methanol.

The conditions of hydroperoxide decomposition will be essentially the same as prior art solid acid decompositions of hydroperoxides except that in general the reaction may be carried out at a higher initial temperature than previously possible since in the present system temperature control is more readily attained and the fear of temperature excursions minimized.

The exothermic decomposition of hydroperoxides can be carried out at temperatures from as low as 25° C. up to about 200° C. Preferably the temperature is maintained as low as possible and especially in the range of 40°–100° C.

The pressure will ordinarily be maintained at atmospheric pressure although it should be high enough to maintain a liquid phase reaction. Where in the broader aspects of the invention, the process is applied to oligomerization of olefins, the feed olefins may be gaseous and the pressure maintained to keep the lowest molecular weight polymer products in the liquid phase.

The present invention is ideally suited for being carried out in a continuous manner with a reactor heat exchanger system. Therewith the hydroperoxide can be continually passed over and in contact with the surface of the thin film or layer of solid polymeric acid catalyst supported on the heat exchanger element and the coolant passed over and in contact with the opposite and heat exchanger side of said element. The amount and volume of coolant to maintain the desired temperature will depend upon the amount of heat generated by the reaction at the acid sites in the catalyst layer as well as the thermal conductivity of the catalyst layer-heat exchanger element system. In each case, optimum conditions will be readily arrived at by one skilled in the art. Since the reaction depends upon the contact of the reactants with the acid sites in the layer of solid polymer acid catalyst, the rate of reaction will be dependant more on the area of the catalyst layer than in the usual terms of catalyst surface/volume ratio. Turbulent flow of reactants at the catalyst surface is thus more desirable than laminar flow.

The decomposition can be carried out in the presence of a solvent. A solvent, however, is not necessary, as it is in prior art processes, to successfully carry out the reaction. The solvent may be any solvent that does not enter into the decomposition and, in the decomposition of peroxides, may be selected from any of those solvents already well known to be useful in the decomposition of peroxides. Acetone is an example of such a solvent and is preferred when cumene hydroxide is decomposed because one of the decomposition products is acetone.

Many variations will be readily apparent without departing from the essential characteristics of the present invention. Thus, in the following examples, the temperatures and pressures employed were such that the active acid catalyst was a surface layer on an unconverted base of the sulfonyl fluoride intermediate which served as a support essentially impermeable to the reactants, the reaction products and the heat transfer fluid or bath of coolant or temperature controlling medium. Other supporting heat exchanger elements such as tubes, sheets, etc. of metal of high thermal conductivity could be advantageously used for more efficient heat removal.

Likewise the process can be carried out advantageously with polymeric acid catalysts other than the preferred substantially perfluoro polymer sulfonic acid. Thus, for example, thin films of copolymers of ethylene and methacrylic acid can be formed on appropriate heat exchanger elements as described hereinabove. Various techniques for applying and forming such thin films can be used such as will be readily apparent to one skilled in the art.

EXAMPLES

The following examples are presented for the purpose of illustration only and are not in any way to be construed as limiting the scope of the invention described herein.

EXAMPLE 1

The sulfonyl fluoride form of the polymer described in Formula III and having an equivalent weight of 1200 formed into a tubing having an inner diameter of 0.024 inches, an outer diameter of 0.036 inches and a length of 18 feet, was immersed in water at 50° C. A mixture of 10% potassium hydroxide, 35% dimethylsulfoxide, and 55% water was pumped through the tubing for 45 minutes. A solution of 2 molar hydrochloric acid was then pumped through the tubing. Before use the reactor was flushed with several reactor volumes (3.2 ml. each) of 10% nitric acid. A thickness of from 0.0011 to 0.0015 inches of the inner wall of the tubing was converted to the sulfonic acid form by this process. The tubing with appropriate flow fittings was suspended in a stirred reaction kettle of distilled water maintained at the desired temperature.

The reactor was equilibrated at the desired flow rate of cumene hydroperoxide and temperature in the stirred reaction kettle until a steady state was obtained. Thereafter the cumene hydroperoxide (no solvent) was pumped through the tubing reactor by a calibrated piston pump, and after at least one reactor volume (3.2 ml) had passed through the reactor at the selected feed rate and temperature in the kettle, samples were collected and analyzed. The results of varying temperature and flow rate are shown in Table I, cumene hydroperoxide being indicated as "CHP":

TABLE I

Acid-Catalyzed Decomposition of Cumene Hydroperoxide in Catalytic reactor-Heat-Exchanger

| Sample Number | T (°C.) | CHP flow rate (ml/min) | Phenol (% w/w) | Cumene (% w/w) | Acetophenon (% w/w) | Alpha-Methylstyrene (% w/w) | $A_{565}$* | CHP** (% w/w) |
|---|---|---|---|---|---|---|---|---|
| 1 | 25.5 | 0.26 | 6.1 | 5.5 | 19.4 | 4.6 | 0.45 | 77. |
| 2 | 31. | 0.26 | 14.3 | 5.6 | 21.6 | 4.9 | 0.34 | 63. |
| 3 | 36. | 0.26 | 15.9 | 5.6 | 19.9 | 4.3 | 0.30 | 53. |
| 4 | 40. | 0.26 | 17.8 | 5.7 | 21.1 | 4.3 | 0.53 | |
| 5 | 45. | 0.26 | 20.2 | 5.4 | 17.6 | 3.6 | 0.18 | |
| 6 | 51. | 0.26 | 25.0 | 5.4 | 16.9 | 3.1 | 0.08 | 31. |
| 7 | 62. | 0.26 | 36.1 | 4.6 | 12.7 | 2.4 | 0.02 | 14. |
| 8 | 73. | 0.26 | 42.6 | 6.9 | 9.2 | 3.1 | 0.005 | 4.3 |
| 9 | 82. | 0.26 | 34.9 | 5.8 | 10.8 | 2.4 | 0.03 | 1.0 |
| 10 | 90. | 0.26 | 40.4 | 6.1 | 9.7 | 2.6 | 0.37 | 5.3 |
| 11 | 91. | 0.13 | 39.3 | 7.4 | 11.4 | 2.8 | 0.37 | |
| 12 | 90. | 0.07 | 43.2 | 6.7 | 8.9 | 3.0 | 0.47 | |
| 13 | 80. | 1.0 | 16.9 | 4.2 | 12.0 | 4.3 | 0.49 | 62. |
| 14 | 80. | 0.51 | 12.6 | 4.6 | 12.8 | 3.3 | 0.56 | 62. |
| 15 | 80. | 0.71 | 8.5 | 4.5 | 15.0 | 4.0 | 0.58 | 80. |
| 16 | 80. | 0.13 | 6.9 | 4.7 | 15.2 | 3.9 | 0.57 | 80. |
| 17 | 80. | 0.07 | 2.7 | 5.1 | 16.4 | 3.9 | | 92. |
| 18 | 80. | 0.26 | 2.8 | 4.4 | 16.6 | 2.3 | | 94. |
| 19 | 80. | 0.26 | 2.0 | 4.5 | 16.8 | 4.0 | | 93. |
| 10% CHP*** | | | .074 | 0.7 | 2.4 | 0.4 | | |
| 10% CHP*** | | | .025 | 0.7 | 2.4 | 0.4 | | |

*observed Absorbance, titration of residual CHP with iodide.
**CHP residual
***in acetone The results are listed in the order actually run; there was no regeneration of the reactor between runs. A total volume of at least 250 ml of neat cumene hydroperoxide was used with an estimated catalyst weight of 0.2-0.3 g. A tan color appeared in the tube inner wall at the highest temperatures (90°); the catalytic activity was considerably diminished after a short period at this temperature (#12 to #19). Regeneration of the catalyst by flushing with a small volume of 30% nitric acid followed by distilled water in the usual manner completely restored catalytic activity. At temperatures of 60°-80°, the catalyst did not exhibit tar formation or diminished activity in extended operation. Cumene and alpha-methylstyrene in the product are seen to be relatively constant; they seem to result principally from factors other than acid-catalyzed decomposition (the results for samples of 10% CHP should be multiplied by 10 for comparison), such as impurities in technical grade cumene hydroperoxide during reaction and gas chromatography. The acetophenone diminishes somewhat with increased acid-catalyzed decomposition, indicating that it is likely a product of both acid-catalyzed and thermal decomposition. Analysis of cumene hydroperoxide was by absorbance, a modification of the iodometric method of Wagner et al (Anal. Chem. 19, 976 (1947)), substituting ethanol for isopropyl alcohol and reading the absorbance of the generated $(I_2+I_3^-)$ at 565 nm (isobestic point).

EXAMPLE 2

Approximately 100 feet of the sulfonyl fluoride polymer described in Example 1 was wound around a solid aluminum spool 3.0 inches in diameter and 10 inches long. The aluminum spool was then cast in acrylic casting resin. Following the procedure of Example 1, a thickness of from 0.0011 to 0.0015 inch of the inner wall of the tubing was converted to the catalytic sulfonic acid form.

Cumene hydroperoxide was introduced at 46° C. at a flow rate of 0.26 ml/min. Sampling of the effluent after steady state was established indicated some residual cumene hydroperoxide. The temperature was raised to 50° C.; after one reactor volume had passed through at this temperature, a preparative sample (of 175.9 g) was taken. Distillation of the sample through a 1×30 cm Vigreaux column yielded the results in Table II.

TABLE II

| Fraction # | Temperature (°C.) Head | Pot | Recovered Wt. (g) | % |
|---|---|---|---|---|
| 1 | 54.5-56.5 | 90-122 | 41.4 | 25.5 |
| 2 | 56.5-145 | 122-172 | 15.1 | 9.3 |
| 3 | 145-156.5 | 172-179 | 13.2 | 8.1 |
| 4 | 156.5-177.5 | 179-185 | 13.2 | 8.1 |
| 5 | 177.5-183 | 185-208 | 60.2 | 37.1* |
| 6 | 183-191 | 208-229 | 4.3 | 2.7 |
| 7 | 191-196 | 229-310 | 11.3 | 7.0 |
| 8 | 196** | 310-360 | 3.4 | 2.1 |
| Pot Residue | | | 6.6 | 4.1 |
| | | | 162.1 g, | |

*joint leaked during this sample
**temperature decreasing
***% based on 162.1 g. recovered.

As indicated by the boiling points, fraction 1 was mostly acetone fractions 3 and 4 mostly acetophenone and cumene and fraction 5 mostly phenol.

EXAMPLE 3

Thirty-three polymer fibers (in the form of the potassium salt of the sulfonic acid described in Formulas I and II and obtained as NAFION resin, a trademarked product of E. I. duPont) of 50 inches length having 0.006 inch diameter, 1200 equivalent weight and a total weight of 6.71 g were suspended inside a 3-foot long polypropylene tube having an outer diameter of ¼ inch and an inner diameter of 0.170 inch. The midpoint of each fiber was looped over a stainless steel wire at the tube entrance. After the attachment of end fittings, the tube was suspended vertically, inlet down, in a 3 liter reaction kettle filled with water stirred at the desired temperature.

The reactor was flushed with 30% nitric acid, followed by flushing with distilled water until the effluent was neutral. The reactor was dried at 45° C. under nitrogen flow.

The water in the kettle was heated to and maintained at 79° C.

Cumene hydroperoxide was introduced at a flow rate of 0.52 ml/min. A total of 100.2 g of effluent was collected in an ice-cooled trap and a portion (99.0 g) was distilled through a 1 cm×30 cm vacuum-jacketed Vigreaux column (725 mm.) to yield the results shown in Table III.

TABLE III

| Friction # | Temperature (°C.) Head | Pot | Wt. (g) | % on (97.2g) |
|---|---|---|---|---|
| 1 | 54.5-55 | 88-109 | 20.7 | 20.3 |
| 2 | 55-65 | 109-114 | 2.8 | 2.8 |
| 3 | 65-170 | 114-193 | 11.5 | 11.8* |
| 4 | 170-178 | 193 | 1.7 | 1.7 |
| 5 | 178-183 | 193-292 | 30.8 | 31.7 |
| 6 | 183-196 | 292-307 | 1.4 | 1.4 |
| 7 Pot Residue | | | 28.3 | |
| | | | 97.2 g | |

*two phases

Nuclear magnetic resonance spectroscopy and infrared spectroscopy on a distilled (0.25 mm, 135°-175°) portion of the pot residue indicated that it consisted largely of isomers of cumylphenol.

EXAMPLE 4

Using the reactor system described in Example 3 immersed in a kettle of water at 63° C., a mixture of cumene hydroperoxide (100.5 parts by wt.) and acetone (99.5 parts by wt.) was pumped through the reactor at a flow rate of 0.56 ml/min until a total of 284.1 g had been collected. Distillation through a 1×30 cm Vigreaux column (730 mm) yielded the results shown in Table IV.

TABLE IV

| | Distillate Fractions From Example 4 | | | | |
|---|---|---|---|---|---|
| Fraction # | Temperature (°C.) Head | Pot | Total Overhead Wt (g) | % (of 284.1 g) | Adjusted % |
| 1 | 56-62 | 66-133 | 168.5 | 59.3 | (19.0) |
| 2 | 62-170 | 133-184 | 23.5 | 8.3 | 16.5 |
| 3 | 170-175.5 | 184-185 | 2.05 | 0.7 | 1.4 |
| 4 | 175.5-182.5 | 185-224 | 57.3 | 20.1 | 40.1 |
| 5 | 182.5-196 | 224-282 | 5.4 | 1.9 | 3.8 |
| 6 Pot Residue | | | 21.4 | 7.5 | 15.0 |
| | | | 278.2 | | |
| | | | −141.3 g | | acetone charged |
| | | | 136.9 g | | recovered product |

Temperature °C.
Pressure 730 mm
*% adjusted to subtract added solvent

Other examples of carrying out the present invention are as follows:

EXAMPLE 5

With a concentric tube arrangement with an inner one-inch O.D. stainless steel tubing having formed on the outside thereof a 0.02 inch layer of the sulfonic acid form of perfluorocarbon polymer described in Example 1 and an outer metal tubing or casing of a diameter to leave therebetween an annular space of 0.05 inch radial distance, a tertiary butyl hydroperoxide will be flowed through the annular space in sufficient volume to maintain the space full and in turbulent flow in contact with the active catalyst surface. At the same time, a coolant such as water or other heat transfer liquid is flowed through the inner tubing in a sufficient amount and volume to remove heat of reaction and maintain the temperature of the mixture of reactants and reaction products at a desired temperature such as, for example, 40° C. The primary products will be acetone and methanol.

EXAMPLE 6

A thin film of polystyrene sulfonic acid catalyst can be prepared by casting a film of polystyrene on a supporting heat exchanger element (formed of metal such as steel roughened to promote the adhesion of the polystyrene). Then the surface of polymer film can be sulfonated with a cosolvent trichloroethylene and 98% sulfuric acid and heating to 100° C. for a period not exceeding one-half hour. The cosolvent and excess sulfuric acid are removed and the surface washed with portions of aqueous sulfuric acid of decreasing strength until the final wash is neutral. Using the resultant heat exchanger element coated with the polystyrene sulfonic acid in the reactor-heat exchanger arrangement described in Example 5, cyclohexyl hydroperoxide can be flowed through the annular space and with an adequate flow of water as coolant in the inner tubing to maintain the temperature at 50°-80° C., the hydroperoxide can be decomposed under controlled conditions to produce a reaction mixture composed mostly of cyclohexanone. A "Nafion" type carboxylate catalyst can be prepared as a film on the steel heat exchange element as follows: the copolymer of tetrafluoroethylene and perfluorovinyl ether methyl ester (in a mol ratio such as to give about 10–30% ester in the copolymer) is applied such as by molding as a thin film on the heat exchanger element. Then the surface is treated with NaOH to saponify the ester groups and then, after washing, is treated with dilute acid to form carboxylic acid groups. (More details are given by Hiroshi Ukihashi in Chemtech February 1980 pp. 118–120.)

I claim:

1. In the process of conducting the exothermic liquid phase decomposition of organic hydroperoxide catalyzed by a solid polymeric acid catalyst to produce ketones and alcohols, the improvement which comprises carrying out said decomposition by passing said hydroperoxide over the surface of a thin film of said acid catalyst which is insoluble in said hydroperoxide and reaction products and which is on the surface of a substantially impermeable heat exchange element and withdrawing heat of reaction by passing a heat transfer fluid over the opposite side of said catalyst-supporting heat exchanger element.

2. The process of claim 1 wherein said catalyst is a substantially perfluorocarbon polymer containing pendant sulfonic acid groups.

3. The process of claim 1 wherein said film has a thickness of up to 10 mils.

4. The process of claim 1 wherein said catalyst-supporting heat exchanger element is a heat conductive metal.

5. The process of claim 1 wherein said catalyst-supporting heat exchanger element is a copolymer of tetrafluoroethylene and a perfluorovinyl ether having pendant sulfonyl fluoride groups.

6. The process of claim 1 wherein said heat transfer fluid is passed over said heat exchanger element at a temperature and rate to remove excess heat and to maintain the reaction temperature between 25° C. and 100° C.

7. The process of claim 2 wherein said catalyst is a copolymer of tetrafluoroethylene and a perfluorovinyl ether having pendant sulfonic acid groups.

8. In the process of conducting the exothermic liquid phase decomposition of cumene hydroperoxide catalyzed by a solid polymeric acid catalyst to produce phenol and acetone, the improvement which comprises carrying out said decomposition by passing said hydroperoxide over the surface of a thin film of said acid catalyst which is isoluble in said hydroperoxide and reaction products and which is on the surface of a substantially impermeable heat exchange element and withdrawing heat of reaction by passing a heat transfer fluid over the opposite side of said catalyst-supporting heat exchanger element.

* * * * *